United States Patent [19]

Igushi

[11] Patent Number: 5,796,480
[45] Date of Patent: Aug. 18, 1998

[54] PARTICLE SIZE DISTRIBUTION ANALYZER WITH FRACTIONATOR PRETREATMENT

[75] Inventor: Tatsuo Igushi, Miyanohigashi-machi, Japan

[73] Assignee: Horiba, Ltd., Kyoto, Japan

[21] Appl. No.: 755,311

[22] Filed: Nov. 22, 1996

[30] Foreign Application Priority Data

Nov. 24, 1995 [JP] Japan .................. 7-329830

[51] Int. Cl.⁶ .................................................. G01N 15/02
[52] U.S. Cl. ................................. 356/336; 250/574
[58] Field of Search ........................... 356/336–338, 356/339–343; 250/574

[56] References Cited

U.S. PATENT DOCUMENTS

| | | | |
|---|---|---|---|
| 4,097,149 | 6/1978 | Aladjem et al. | 356/341 |
| 4,565,448 | 1/1986 | Abbott et al. | 356/339 |
| 4,939,081 | 7/1990 | Figdor et al. | 356/339 |
| 5,087,823 | 2/1992 | Silvy et al. | 356/336 |
| 5,530,540 | 6/1996 | Wyatt et al. | 356/338 |

Primary Examiner—Frank G. Font
Assistant Examiner—Jason D. Vierra-Eisenberg
Attorney, Agent, or Firm—Price, Gess & Ubell

[57] ABSTRACT

Particle size distribution measuring equipment includes a flow cell that can be illuminated with light so that suspended particles can scatter the light and thereby measure both particle size and frequency. A dispenser unit is connected to the flow cell for delivering a sample. A fractionator unit can pretreat the sample to provide particles over a predetermined size in a sealed chamber resulting from the impact of compressed air. The fractionated sample can be delivered to the dispenser, and a controller can automatically coordinate the preparation of the dispenser unit, the flow cell, the measuring of scattered light, and the release of the fractionated sample from the sealed chamber.

10 Claims, 3 Drawing Sheets

5,796,480

1

PARTICLE SIZE DISTRIBUTION ANALYZER WITH FRACTIONATOR PRETREATMENT

BACKGROUND OF THE INVENTION

1. Field of the Invention

The present invention is directed to particle size distribution measuring equipment and method that permit samples of fine particles such as powders and mist to flow into a measuring flow cell and to be measured to determine a particle size distribution in the sample and, more particularly, to a granular sample pretreatment fractionator to ensure a fluid distribution characteristic to the sample.

2. Description of Related Art

The measurement of particle distributions of fine particles such as powders and mist has been automated in recent years. An example of such a system is shown in FIG. 2, which schematically illustrates the principle components of conventional dry particle size measurement equipment for carrying out measurements. A sample feeder portion 33 can feed a specific amount of measuring sample S to an orifice 31 of an injector-type dispenser 32. The dispenser 32 includes an orifice 31 positioned in a sample feeding cylinder 30 which receives compressed air, ca. to thereby permit the measuring sample S to be dispersed by this dispenser 32 and to flow into a measuring cell 35 of an optical measuring portion 34 of the instrument. The measuring sample S is recovered after it passes through the measuring cell 35 by a suction device 36.

In the configuration of the conventional example of FIG. 2, even when measuring samples S having a greatly varying degree of coagulation are mixed in the sample feeder portion 33, they must be mechanically fed from the sample feeder portion 33 to the dispenser 32 in a specified amount. Depending on the coagulation of the sample, the dispersing capability of the dispenser 32 can be significantly degraded. Sometimes measuring samples S with a large coagulation propensity will even be introduced into the measuring cell 35 without being properly dispersed, and thereby will adversely influence the measurement. Consequentially, the conventional measuring equipment has a problem of reproducing such a measurement and can be unable to carry out highly accurate particle size distribution measurements. This problem can be further exacerbated when the spouting outlet of the orifice 31 composing the dispenser 32 is fitted with a small-caliber diameter outlet in the range of 200–300 μm. Thus, when measuring samples with a particle size larger than the caliber size are mixed, the orifice 31 can be readily clogged and measurement can be interfered with.

Thus, the prior art is still seeking to optimize and facilitate the measurements of samples and, particularly, samples that may have a propensity for coagulation.

OBJECTS AND SUMMARY OF THE INVENTION

It is an object of the present invention to provide particle size distribution measurement equipment which can select, disperse, and supply measuring samples of a specified particle size for measurement and to carry out highly accurate particle size distribution measurements.

It is another object of the present invention to provide a method and apparatus to pretreat a sample in a fractionator unit that can be automatically integrated into the measurement cycle.

The particle size distribution measuring equipment of the present invention includes a fractionator unit having a sealed

2 chamber with a support surface at the bottom of the chamber for supporting a sample that can be arranged appropriately within a sample cup container. An air-injecting nozzle member can be suspended from a roof member of the chamber and directed at the sample. The nozzle member can be connected to a controlled source of fluid such as compressed air to thereby emit compressed air so that it will directly impact the sample and dilute it within the volume of the sealed chamber. The particles in the sample can impact the chamber walls to disperse any coagulated lumps and to permit larger particles to settle on the support surface of the chamber so that a predetermined range of particles can reach a predetermined concentration with the air. A transfer conduit is connected to the sealed chamber, for example, with a port mounted in the roof member. A valve downstream of the sealed chamber can be controlled to automatically opened to permit the fractionated and diluted sample to be connected to a dispenser unit. The dispenser unit can then transmit a controlled amount of the sample to a measurement flow cell whereby a source of light such as a laser can irradiate the air suspended particles with the light being scattered at various angles. A detector unit, which can comprise a series of side, rear, and forward detectors such as a ring-type detector, can measure the impact of light and thereby determine both the particle size and the frequency that these particle sizes are experienced in the sample. For example, a frequency/cumulative distribution graph with overlapping curves can be calculated and appropriately displayed. The source of light can alternatively be a plurality of sources of light so that different wavelengths of irradiating light can be used to accommodate different sizes of particles. For example, the light can include a short wavelength tungsten lamp in addition to a helium neon laser beam.

A dry dispenser that is connected via the transfer conduit can also be fed with compressed air to regulate the flow of the diluted sample into the measurement flow cell. The fractionator unit or granular sample generator comprises a hermetically sealed container for storing samples so that they can be delivered to the orifice of the dry dispenser. If the sample to be stored in the hermetically sealed container are powder, the powder can be both scattered and floated by the compressed air sprayed from the nozzle. Of the particles contained in the sample, only those samples smaller than a specified particle size which do not settle on the chamber bottom are fed in a specified amount to the dry dispenser. The samples are subsequently dispersed and fed into the measurement flow cell so that the disbursing capability of the disperser is not degraded and the disperser will not be clogged with sample particles whereby the measuring reproducibility will be improved. In addition, a highly accurate particle size distribution measurement can be achieved. A controller can coordinate the automatic operation of the equipment.

The present invention can also work with liquid samples. Because of the design of the hermetically sealed container for storing the samples, a mist or aerosol can be generated by spraying the compressed air into a liquid sample from the nozzle, thereby suspending and floating droplets of the liquid. Only those droplets smaller and lighter than a specified particle size will not settle on the container bottom and will be fed into the dry dispenser in a predetermined specified amount. The aerosol will be dispersed and introduced into the measurement flow cell so that a highly accurate particle size distribution can be measured in a similar manner to that of the dry powder.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DETAILED DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide a particle size distribution analyzer with a fractionator pretreatment and automatic method of measurement.

Figure 1:
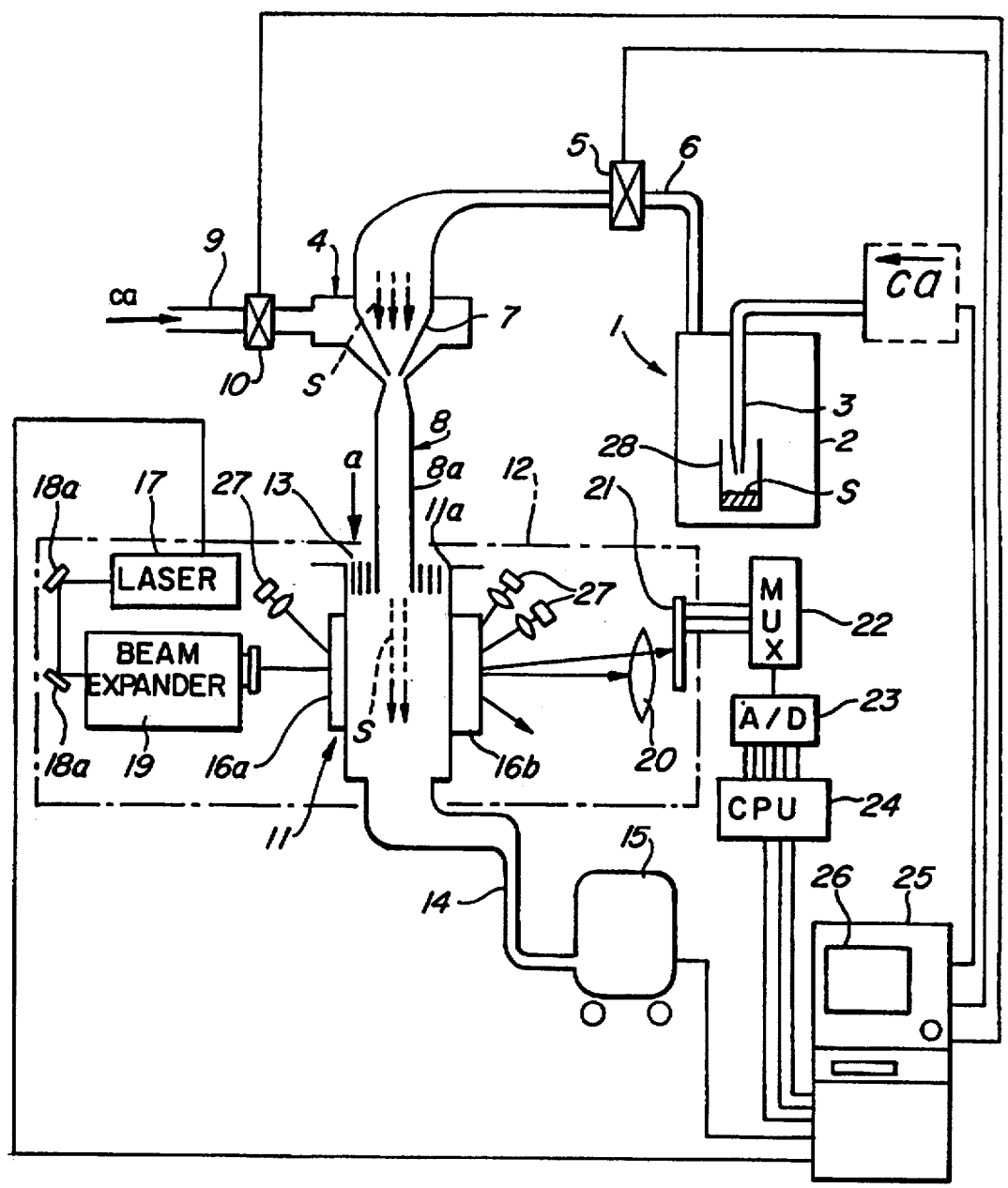
FIG. 1 is a schematic illustration of particle size distribution measuring equipment incorporating a fractionator unit according to the present invention.
Figure 2:
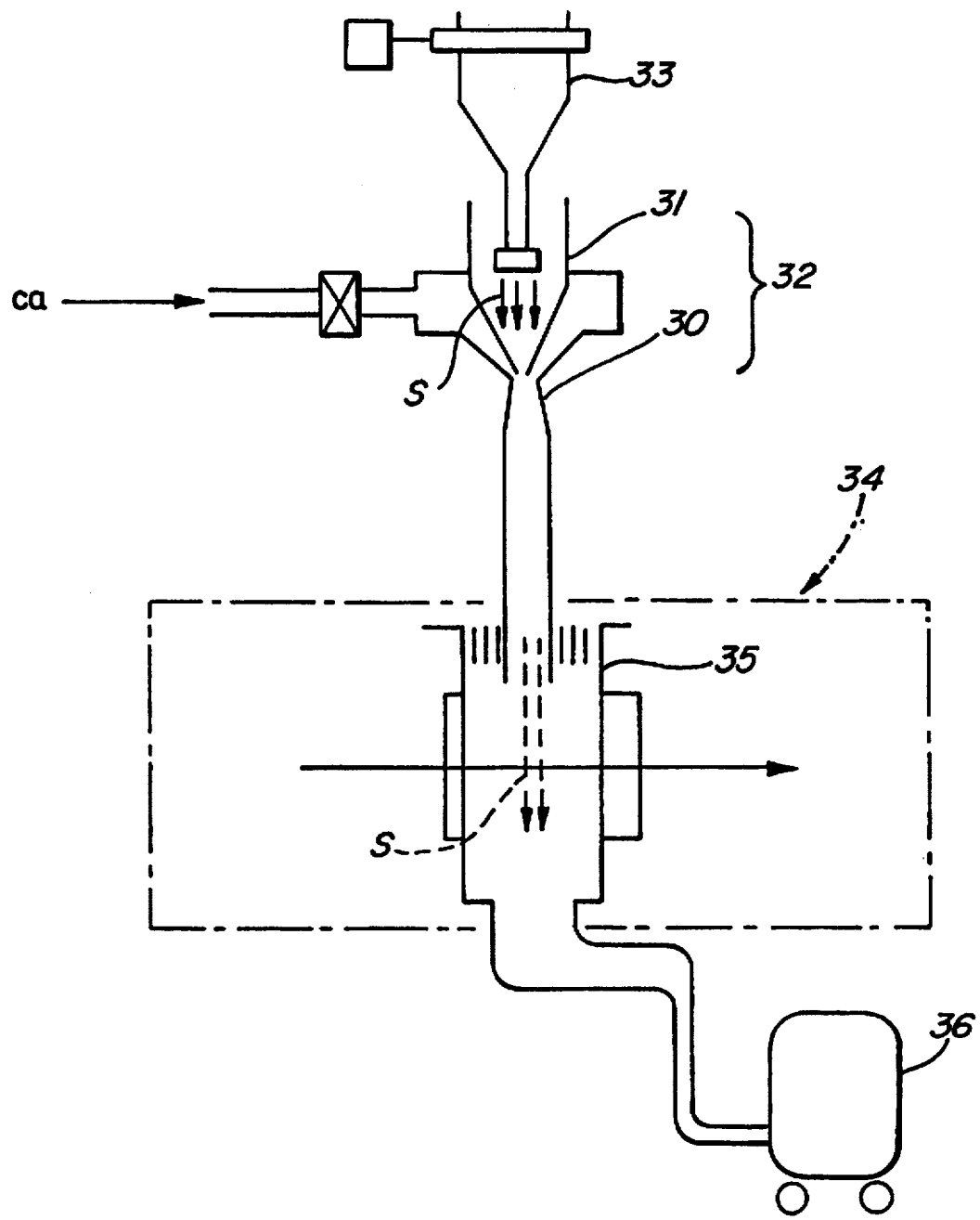
FIG. 2 is an illustration of conventional particle size distribution measuring equipment.

FIG. 1 shows one example of particle size distribution measuring equipment according to the present invention. A granular sample generator or fractionator unit 1 is schematically disclosed. When the sample is of a powder configuration, it can serve as a fractionator for fractionating the samples into large particle sizes and small particle sizes. In the case of a liquid sample, it can serve as an aerosol generator which can make the liquid sample into an aerosol and, at the same time, serve as a fractionator to fractionate the generated aerosol into large droplet sizes and small droplet sizes.

The fractionator unit 1 includes a hermetically sealed container 2 having an upper roof member and a lower support surface for storing a measuring sample S. An injector nozzle 3 can be suspended from the roof member to face directly downward above a sample container for spraying compressed air, ca. to impact the sample S. The hermetically sealed container 2 can have a door on the side or the bottom that can be opened and appropriately sealed and closed for permitting the introduction of the measuring sample S in a cup 28. The volume of the sealed chamber is significantly larger than the amount of the sample that will be positioned beneath the nozzle 3. Thus, when compressed air impacts on the sample, it will fluidize the specimen with the air as the carrier medium so that the lighter particles can be separated and removed from the sealed chamber through a transfer conduit 6. As can be appreciated, the volume of the chamber, the flow of the compressed air, and the particle size can be appropriately balanced to provide a predetermined fluidization of the sample and the carrier air.

The transfer conduit 6 contains a valve 5 that controls the communication of the fractionated sample to the dry dispenser 4. The valve 5 can be automatically opened and can further meter the flow through the transfer conduit 6. The dry dispenser 4 takes in the sample and disperses the sample to the measurement flow cell 11. The dry dispenser 4 can be constructed by providing an orifice 7 at the top of a sample feeding cylinder 8. The orifice 7 is in free communication with the hermetically sealed container when the valve 5 is open. The top of the sample feeding cylinder 8 receives compressed air from a pipe 9 through a valve 10 that can also be automatically controlled. The compressed air creates a venturi effect to draw the sample into the feeding cylinder 8.

The lower half of the sample feeding cylinder 8 constitutes a small caliber portion 8a. The flow measuring cell 11 is positioned vertically beneath the sample feeding cylinder 8 in an optical chamber 12 to constitute an optical measuring portion.

At the top end of the flow cell 11 is a baffled aperture 11a with the lower half of the small caliber portion 8a of the sample feeding cylinder 8 aligned in the center of the aperture 11a. The baffle plates 13 permit atmospheric air to flow into the flow cell 11. The lower portion of the flow cell is reduced in size to form a conduit 14 connected to an air suction device 15 such as a pump. Windows 16a and 16b are provided on the flow cell 11 downstream from the sample feeding cylinder 8. An He-Ne laser device 17 is provided and is positioned in such a manner that the laser beam impinges a series of reflecting mirrors 18a and 18b. The laser beam then enters into a beam expander 19 arranged opposite to the window 16a. The expanded laser beam then penetrates through the window 11a into the measuring flow cell 11. The laser light will irradiate the particles in the flow measuring cell 11 so that they will be scattered at various angles. If the particles are large, the scattering is concentrated in the forward direction. Conversely, if the particles are small, the scattering will be in all directions. To measure larger particles, data on the scattered light intensity at a small angle is acquired, for example, as the light enters the condenser lens 20 after it has departed from the window 16b. The photodetector 21 will detect light which has passed through the flow cell 11 and can, for example, comprise an arrangement of photodiodes in a ring form. Additional detectors 27 are arranged both on the side and rear of the flow cell relative to the detector 21. These detectors provide data on the intensity of large angle scattering which is necessary to measure smaller particles. From the angular measurement of the scattered light by all these detectors, the particle distribution can be calculated based on the Mie theory. The light data detected by the photodetectors can be applied to CPU 24 via multiplexer 22 and an A/D converter 23. A controller 25 receives the processed data and a display screen 26 can display the particle size distribution measured based on the detected data. The controller 25 not only can carry out processing of the particle size distribution, but also can control the mechanical portions of the instruments such as the opening and closing of the valves 5, 10, the driving of the air sucking device 15, and the introduction of compressed air into the chamber 2. While not shown in the schematic of FIG. 1, the various photodetectors 27 can comprise a plurality of photodiodes, and their outputs can also be inputted through the multiplexer 22 and the A/D converter 23 to, respectively, the computer 24 and then the controller 25.

Figure 3:
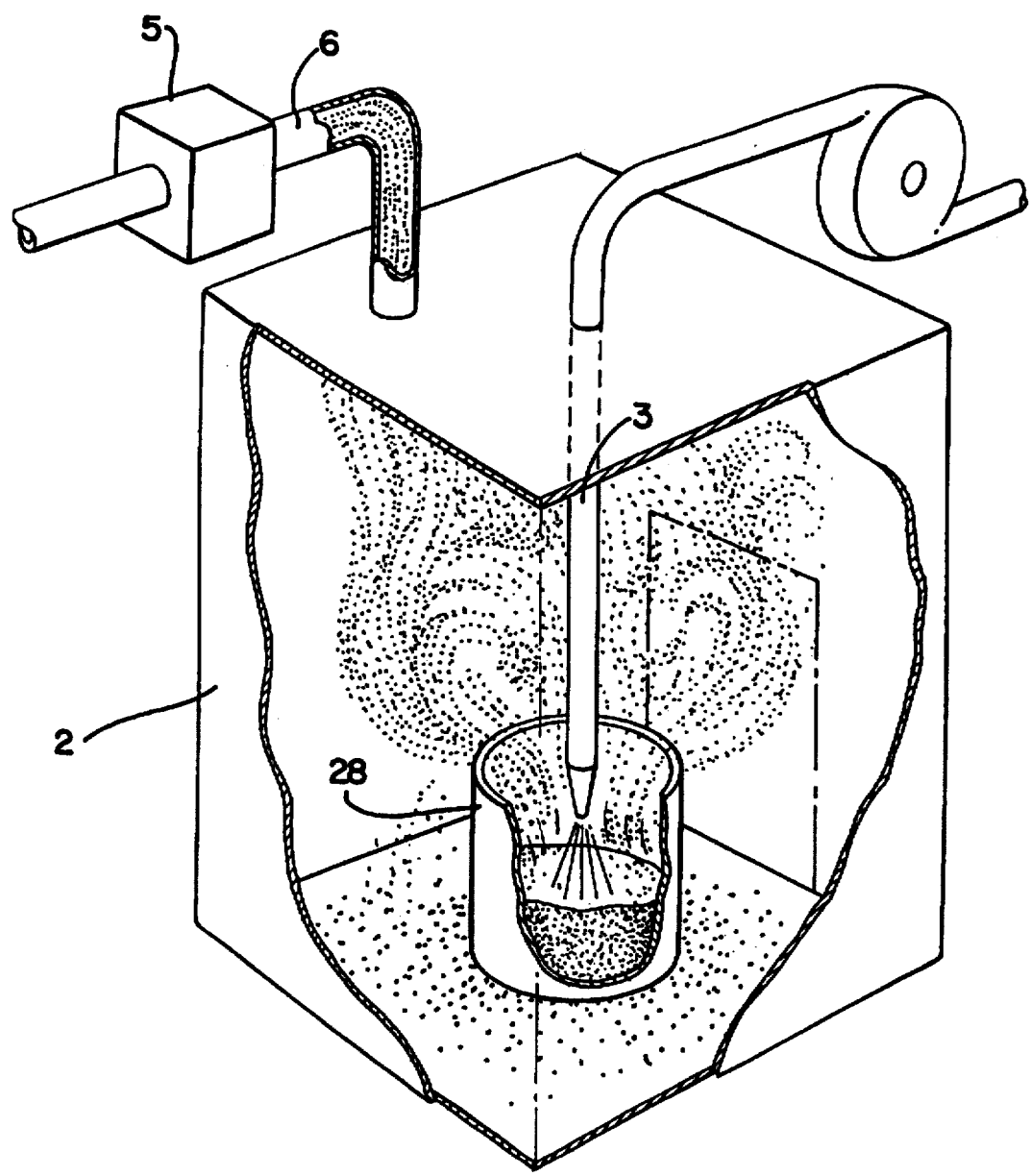
FIG. 3 is a schematic illustration of a fractionator unit.

In operation, an operator can use, for example, a small container 28 containing the measurement sample S and place it on the support surface within the hermetically sealed container 2, for example, as shown in FIG. 3. The container 28 is positioned and stored at a location opposite to the nozzle 3 for delivering of the compressed air, ca. The controller 25 can activate the air sucking device 15, and atmospheric air will be sucked through the aperture portion 11a at the top end of the measuring flow cell 11 into the interior of the flow cell 11. This will further generate a baffled air stream in the flow cell 11 by the operation of the baffle plate 13 provided at the aperture portion 11a. The controller 25 can then cause the compressed air to flow through the nozzle 3 with the valve 5 closed. Compressed air will be ejected from the nozzle 3 within the granular sample generator/fractionator 1.

If the measuring sample S is powder, the powder will be blown by the compressed air, ca, to permeate inside of the hermetically sealed container 2 that stores the sample. Larger particle sizes, that is, those having a large coagulation degree, contained within the granular measuring sample S, will settle faster on the bottom of the container 2. Therefore, at the upper part of the container 2, measuring samples of particles that are smaller than the predetermined specified particle size will float or be fluidized, and thereby a fractionation of the measuring sample will occur in a vertical direction.

If the measuring sample is in a liquid state, the compressed air will contact the liquid and create an aerosol effect which will likewise permeate the interior of the hermetically sealed container 2. The aerosol generated in this way is also fractionated vertically into large particle sizes and small particle sizes in a manner similar to that of the powder sample.

The controller 25 can open the valve 10 that permits compressed air to flow from the compressed air feeding tube 9 into the sample feeding cylinder 8 of the dry dispenser 4. When this occurs, the pressure inside the sample feeding cylinder 8 will become negative. The controller 25 can then open the valve 5 to permit a free communication between the orifice 7, the dry dispenser 4, and the hermetically sealed container 2 of the granular sample generator/fractionator 1. The measuring sample S smaller than the predetermined specified particle size that has been fractionated and is floating at the upper portion of the inside of hermetically sealed container 2 will be fed through the transfer conduit 6 to the orifice 7 of the dry dispenser 4. Thus, the fractionated sample of a specified quantity will be sprayed and dispersed in the sample feeding cylinder 8 as a result of the negative pressure condition.

The measuring sample S that is now dispersed in the dry dispenser 4 is aligned in the feeding cylinder 8 and introduced into the measurement flow cell 11. After interacting with the measurement light, for example, a laser beam, it will be subsequently recovered in the air sucking device 15 after it passes through the tube 14.

As the measuring sample S falls downward in the flow cell 11, the laser beam from the helium neon laser 17 will interact and be scattered to be accordingly detected by the photodetector sensors 21–27. The detection outputs from these photodetector sensors are processed and eventually provided to the controller 25 so that the particle size distribution can be computed and displayed. After completion of the measurement cycle, the feed of the compressed air, ca, to both the granular sample generator/fractionator 1 and the dry dispenser 4 is terminated by the controller 25.

Since the measuring sample is fractionated into particles smaller than a predetermined size, that being the coagulated particles that will settle on the bottom of the fractionator 1, then an advantageous measuring sample will be delivered to the dry dispenser 4 in a specified flow amount rate, which can be controlled by automatically metering the opening of the valve 5. The capability of dispensing through the dry dispenser 4 will not be degraded, nor will the dry dispenser become clogged with the measuring sample S. Accordingly, the measuring reproducibility will be improved. Additionally, because the measuring sample S is smaller than the predetermined size, a highly accurate particle size distribution can be computed.

The granular sample generator/fractionator unit 1 could likewise control the quantity and cycle of application of compressed air, ca, through the controller 25 to optimize the impact of the compressed air through the nozzle 3 onto the sample S. When the sample is powder, it can be blown about the interior of the hermetically sealed container 2, which is significantly larger than the volume of the sample cup 28. Thus an environment will be provided that enhances the capability of only the smaller particles beyond the predetermined size to be fractionated in the upper part of the sealed chamber and ultimately fed to the dry dispenser 4 in a specified amount for dispersion and treatment through the valved transfer conduit 6.

Likewise, if the sample is liquid, the same apparatus can be used, and the sample can be blown into an aerosol configuration by the compressed air sprayed from the nozzle 3 so that only liquid particles in the sample smaller than a specified size would fractionate at the upper part of the chamber and again be fed to the dispenser 4 through the transfer conduit 6. In both cases, a highly accurate particle distribution measurement can be made as a result of the fractionator pretreatment.

As can be appreciated, while the controller 25 is used to control the sequence of applications of compressed air, valve openings, and the suction device, a separate controller or the computer 24 could be appropriate configured to perform these tasks. Additionally, the hermetically sealed container 2 can be further modified to facilitate the fractionating of the sample. Finally, other sources of light could be utilized in the flow measurement cell.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. Particle size distribution measuring equipment comprising:
   a source of compressed gas;
   a fractionator unit having a sealed chamber with a support surface for supporting a sample, a nozzle member connected to the source of compressed gas and directed at the sample support surface to emit compressed gas, the volume of the sealed chamber being larger than the samples, the compressed gas can dilute the sample in the chamber to a predetermined concentration with the gas;
   a conduit connected to the sealed chamber;
   a disperser unit connected to the conduit;
   a flow cell connected to the disperser;
   a source of light for illuminating the flow cell;
   a detector unit positioned adjacent the flow cell for measuring the light scattered by the particles in the sample; and
   means connected to the detector unit to calculate the particle size distribution.

2. The invention of claim 1 further including a valve member for controlling flow through the conduit.

3. The invention of claim 1 wherein the chamber has an upper roof member and the nozzle member is mounted to be suspended from the roof member above the sample support surface, the conduit having an opening in the roof member.

4. In particle size distribution measuring equipment for measuring particle sizes of samples delivered to a sample cell, the improvement comprising:
   a fractionator assembly including a sealed chamber, means for supporting a sample, means for injecting compressed gas into the sample to disperse the sample in the sealed chamber and permit portions of the sample to be separated, and means for transferring the dispersed sample that is not separated and gas from the sealed chamber to the sample cell.

5. The invention of claim 4 wherein the means for injecting compressed gas includes a nozzle for directing a stream of compressed gas into the sample.

6. The invention of claim 5 wherein the sealed chamber has an upper roof member and a lower support floor member, the sample is supported on the floor member, the nozzle is directed downward from the roof member towards the sample, and the means for transferring includes a conduit connected to the roof member for egressing diluted sample through the roof member, while the separated portions of the sample settle on the lower support floor member.

7. The invention of claim 6 wherein the means for transferring includes a valve for controlling fluid through the conduit.

8. A method for measuring a sample of fine particles or mist by detecting light scattered from the sample when it is disbursed in a fluid comprising the steps of:

introducing a sample into a sealed chamber;

automatically impacting the sample with a stream of gas of sufficient force to disburse the sample about the interior of the chamber and to fractionate the sample above a predetermined size;

automatically providing a negative pressure to a dispenser connected to the sealed chamber;

automatically providing a negative pressure to a measurement flow cell connected to the dispenser;

automatically releasing the fractionated sample from the sealed chamber to the dispenser;

automatically applying light to the measurement flow cell; and automatically measuring the sample in the flow cell from the light scattered by the sample.

9. The method of claim 8 further including settling a portion of the sample above the predetermined size at a lower portion of the sealed chamber.

10. Particle size distribution measuring equipment comprising:

a source of compressed gas;

a fractionator unit having a sealed chamber with a support surface for supporting a sample, a nozzle member directed at the sample support surface and adapted to emit compressed gas, the volume of the sealed chamber being larger than the sample whereby the compressed gas can dilute the sample in the chamber to a predetermined concentration with the gas;

a conduit connected to the sealed chamber;

a disperser unit connected to the conduit;

a flow cell connected to the disperser;

a source of light for illuminating the flow cell;

a source of light for illuminating the flow cell;

a detector unit positioned adjacent the flow cell for measuring the light scattered by the particles in the sample;

calculator means connected to the detector unit to calculate the particle size distribution; and a controller for automatically impacting the sample with a stream of compressed gas for automatically providing a negative pressure to the disperser unit and the flow call, for automatically releasing the sample after it has been fractionated in the sealed chamber, for automatically applying light to the flow cell and for automatically activating the calculator means to calculate the particle size distribution from the light measured by the detector unit.

* * * * *